United States Patent [19]

Schulz et al.

[11] Patent Number: 5,370,688
[45] Date of Patent: Dec. 6, 1994

[54] ENCAPSULATED GEL BREAST PROSTHESIS AND METHOD OF MAKING

[75] Inventors: Michael W. Schulz; Robert E. Shaw, both of Waco, Tex.

[73] Assignee: Spenco Medical Corporation, Waco, Tex.

[21] Appl. No.: 39,651

[22] Filed: Mar. 30, 1993

[51] Int. Cl.$^5$ .............................. A61F 2/52; A61F 2/54
[52] U.S. Cl. ............................................. 623/7; 623/66; 623/901
[58] Field of Search ........................ 623/7, 8, 66, 901

[56] References Cited

U.S. PATENT DOCUMENTS

| | | | |
|---|---|---|---|
| 3,196,464 | 7/1965 | McKee | 3/36 |
| 3,401,407 | 9/1968 | Pittman | 3/36 |
| 3,576,037 | 4/1971 | Klein | 3/36 |
| 3,641,592 | 2/1972 | Den Bleyker | 3/36 |
| 3,663,968 | 5/1972 | Mohl et al. | 3/36 |
| 3,706,104 | 12/1972 | Dehlin et al. | 3/36 |
| 3,795,921 | 3/1974 | Zucker | 3/36 |
| 3,811,133 | 5/1974 | Harris | 3/36 |
| 3,845,507 | 11/1974 | Kirby et al. | 3/36 |
| 3,852,833 | 12/1974 | Koneke et al. | 3/36 |
| 3,858,248 | 1/1975 | Crowe | 3/36 |
| 3,896,506 | 7/1975 | Hankin et al. | 3/36 |
| 3,911,503 | 10/1975 | Hankin | 3/36 |
| 3,960,786 | 6/1976 | Akiyama | |
| 4,019,209 | 4/1977 | Spence | 3/36 |
| 4,023,575 | 5/1977 | Nixon | 128/481 |
| 4,086,666 | 5/1978 | Vaskys et al. | 3/36 |
| 4,100,627 | 7/1978 | Brill, III | 3/36 |
| 4,125,117 | 11/1978 | Lee | 128/481 |
| 4,172,298 | 10/1979 | Rechenberg | 3/36 |
| 4,195,639 | 4/1980 | Lee | 128/481 |
| 4,199,825 | 4/1980 | Knoche | 3/36 |

(List continued on next page.)

FOREIGN PATENT DOCUMENTS

| | | | |
|---|---|---|---|
| 1199451 | 1/1986 | Canada | 3/36 |
| 0005275 | 12/1982 | European Pat. Off. | |
| 433636 | 12/1991 | European Pat. Off. | 3/36 |
| 465816A | 1/1992 | European Pat. Off. | 128/481 |
| 2487191 | 7/1980 | France | |
| 2451738 | 12/1980 | France | 3/36 |
| 2827076 | 12/1979 | Germany | |
| 2827077 | 1/1980 | Germany | 3/36 |
| 3336279 | 5/1985 | Germany | 3/36 |
| 3416240 | 11/1985 | Germany | 3/36 |
| 2121291B | 12/1983 | United Kingdom | 3/36 |
| 2243324A | 10/1991 | United Kingdom | 128/481 |
| 86/01997 | 4/1986 | WIPO | 3/36 |
| 87/06818 | 11/1987 | WIPO | 3/36 |

*Primary Examiner*—Randall L. Green
*Assistant Examiner*—Dinh X. Nguyen
*Attorney, Agent, or Firm*—Richards, Medlock & Andrews

[57] ABSTRACT

An encapsulated gel breast prosthesis and method of manufacturing therefor is provided wherein a nipple/areola member and gelled breast body are disposed within an inner skin and outer skin which define the exterior shape of the breast prosthesis. The nipple/areola member has a shape, color and hardness simulating the natural shape, color and hardness of a human breast. The encapsulated gel breast prosthesis is fabricated by forming an outer skin and an inner skin. The outer skin is shaped to simulate the natural contour of a woman's breast and includes a region corresponding to the nipple and areola of the breast. A nipple/areola member having a shape, color and hardness, which simulates the natural shape, color and hardness of a woman's nipple and areola is disposed between the outer and inner skins which are then sealed together along their peripheries. This forms a capsule with the nipple/areola member enclosed therein. The capsule is then filled with a gel-forming composition through an opening in the capsule. The opening is sealed and the gel-forming composition is cured into a gel with the nipple/areola member adjacent to the nipple and areola portion of the outer skin.

7 Claims, 2 Drawing Sheets

U.S. PATENT DOCUMENTS

| | | | |
|---|---|---|---|
| 4,227,536 | 10/1980 | Shimenkov et al. | 128/479 |
| 4,245,644 | 1/1981 | Evans | 128/476 |
| 4,247,351 | 1/1981 | Rechenberg | 156/221 |
| 4,249,975 | 2/1981 | Rechenberg | 156/245 |
| 4,258,442 | 3/1981 | Eberl | 3/36 |
| 4,317,241 | 3/1982 | Knoche | 3/36 |
| 4,356,573 | 11/1982 | Knoche | 3/36 |
| 4,364,880 | 12/1982 | Howse | 264/28 |
| 4,366,583 | 1/1983 | Prahl | 3/36 |
| 4,369,792 | 1/1983 | Miller | 128/479 |
| 4,380,569 | 4/1983 | Shaw | 428/283 |
| 4,401,492 | 8/1983 | Pfrommer | 156/61 |
| 4,426,742 | 1/1984 | Prahl | 3/36 |
| 4,573,999 | 3/1986 | Netto | 623/7 |
| 4,600,551 | 7/1986 | Erb | 264/222 |
| 4,605,412 | 8/1986 | LaForest et al. | 623/8 |
| 4,671,255 | 6/1987 | Dubrul et al. | 623/7 X |
| 4,676,795 | 6/1987 | Grundei | 623/8 |
| 4,681,587 | 7/1987 | Eberl et al. | 623/7 |
| 4,701,230 | 10/1987 | Loi | 156/145 |
| 4,778,465 | 10/1988 | Wilkins | 623/7 |
| 4,787,905 | 11/1988 | Loi | 623/7 |
| 4,795,464 | 1/1989 | Eberl et al. | 623/8 |
| 4,826,501 | 5/1989 | Grundei | 623/8 |
| 4,828,559 | 5/1989 | Greenberg | 623/7 |
| 4,950,291 | 8/1990 | Mulligan | 623/8 |
| 5,035,758 | 7/1991 | Degler et al. | 156/61 |
| 5,066,302 | 11/1991 | Rice | 623/7 |
| 5,071,433 | 12/1991 | Naestoft et al. | 623/7 |
| 5,092,881 | 3/1992 | Weber-Unger et al. | 623/8 |
| 5,092,882 | 3/1992 | Lynn et al. | 623/8 |

ENCAPSULATED GEL BREAST PROSTHESIS AND METHOD OF MAKING

FIELD OF THE INVENTION

The field of the invention is that of human body prosthetics and more particularly an encapsulated breast prosthesis and method of fabrication therefor.

BACKGROUND OF THE INVENTION

Breast prostheses are usually made of a synthetic silicone resin that cures to a gelatinous state, and the outer surface of the prosthesis is shaped so as to simulate the shape of a woman's natural breast. As disclosed in U.S. Pat. No. 5,035,758 to Degler, a distinction is made between film-free breast prostheses and prostheses encapsulated or sheathed in film. Film-free breast prostheses have the disadvantage that silicone oil often seeps from the prosthesis. In order to overcome this disadvantage, breast prostheses have been encapsulated in thermoplastic films such as polyurethane films. In general, such breast prostheses are produced by placing the uncrosslinked silicone resin composition together with the crosslinking agent and a catalyst between two flat films that form an envelope for the prosthesis. The films are welded together along this edge except for a small filling opening. The films are then fixed at the edge of a cavity in the area of the welded edge in a die that corresponds to the shape of the breast. Silicone resin composition is added until the films are pressed against the walls of the die cavity, the film edges are then welded together in the area of the filling opening, and the silicone resin composition is cured to form a gelatinous mass. Breast prostheses of this type are described, for example, in U.S. Pat. No. 5,035,758 to Degler.

However, while known film encapsulated breast prostheses simulate the shape of the breast, they do not adequately simulate the natural shape, color and hardness of the areola and nipple regions of a human breast. The present invention provides an improved encapsulated gel breast prosthesis having a nipple and areola which simulates the natural nipple and areola in shape, color and hardness and provides a process for producing a breast prosthesis having such characteristics so as to provide a prosthesis which closely simulates a woman's natural breast.

SUMMARY OF THE INVENTION

A primary object of the present invention is to provide an encapsulated gel breast prosthesis which most closely simulates a natural human breast. The prosthesis has a nipple and areola shaped member having a color and feel which corresponds to the color and feel of a human nipple and areola. The encapsulated gel breast prosthesis comprises an outer skin of flexible material having a shade which corresponds to the shape of a natural human breast including a portion which corresponds to the shape of a nipple and areola, and an inner skin also made of flexible material. The outer and inner skins are sealingly attached to one another along their peripheries, thereby creating a capsule defined by the outer and inner skins. Disposed within the capsule is a nipple/areola member having a desired color and hardness so as to simulate the natural color and hardness of a human nipple and areola. The nipple/areola member has a convex side with a nipple protruding therefrom positioned adjacent to the portion of the outer skin which corresponds to the shape of a nipple and areola. Also disposed within the capsule is a gelled body, such as silicone gel, which fills the remainder of said capsule.

A further object of the present invention is to provide a method of manufacturing the novel encapsulated gel breast prosthesis. In accordance therewith, an outer skin of flexible material is formed. The outer skin is shaped to correspond to the shape of a human breast, including a region which corresponds to the shape of a nipple and areola. An inner skin of flexible material is also formed. A nipple/areola member having a color and hardness simulating the natural color and hardness of said nipple and areola of a human breast is provided. The nipple/areola member has a convex side with a nipple protruding therefrom. The inner and outer skins are sealed together about their peripheries with the nipple/areola member disposed therebetween to form a capsule with the nipple/areola member being therein. The capsule is then filled with a gel-forming composition through an opening in the capsule. The opening is sealed and the gel-forming composition is cured with the convex side of the nipple/areola member positioned adjacent to the nipple and areola region of the outer skin.

A further object of the present invention is to provide an encapsulated gel prosthesis manufactured in accordance with the method steps set forth herein.

Other objects, features and advantages will be apparent from the following description of preferred embodiments of the present invention, given for the purpose of disclosure and taken in conjunction with the accompanying drawings.

BRIEF DESCRIPTION OF THE DRAWINGS

For a more complete description of the present invention and the advantages thereof, reference is now made to the following description taken in conjunction with the accompanying drawings in which.

DETAILED DESCRIPTION OF A PREFERRED EMBODIMENT

Figure 1:
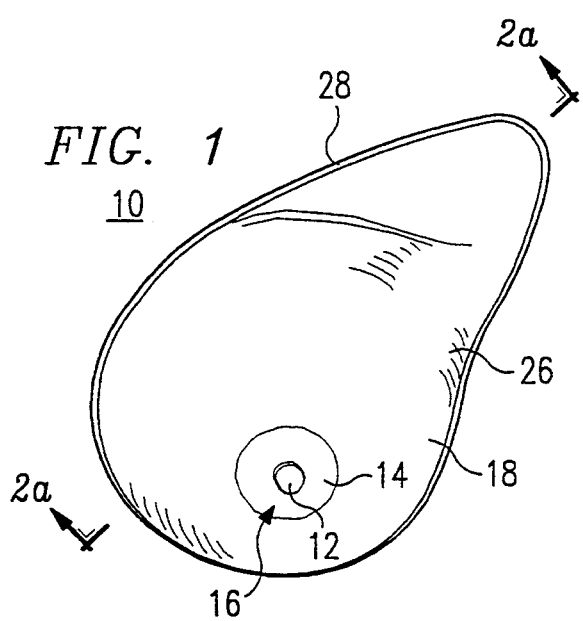
FIG. 1 is a perspective view of the breast prosthesis embodying the present invention.

This invention pertains to a human breast prosthetic and a method of making a film encapsulated breast prosthesis with a color and hardness differentiated, prominent, clearly defined nipple and areola. Referring to FIGS. 1 and 2A, a breast prosthesis 10 is illustrated having a protruding nipple 12 and an areola 14 (hereinafter collectively referred to as the "nipple/areola member" and referenced in the drawings as numeral 16) and a gelled body 18. The nipple/areola member 16 is formed of a material which in the finished product has a color and hardness so as to simulate the natural color and hardness of a nipple and areola of a human breast and which readily distinguishes it from the gelled body 18 of the breast prosthesis 10 which simulates the color and feel of a body of a human breast. Preferably, the nipple/areola member 16 is substantially convex-concave in shape as shown in FIG. 2A. Specifically, the nipple/areola member 16 has a concave side 20 which faces inwardly adjacent to the gelled body 18 and has a convex side 22 which faces outwardly from said gelled body 18 with the nipple 12 protruding therefrom. The body 18 and nipple/areola member 16 are encapsulated between inner skin 24 and outer skin 26 which are sealed together along their peripheries 28. In use, the inner skin 24 is placed adjacent to the user's body and therefore is preferably shaped so as to suitably fit the chest area of the body where the natural breast was removed. The outer skin 26 is shaped so as to simulate the shape and contour of a woman's natural breast, and includes a portion or region 30 shaped to simulate a natural nipple and areola. The convex side 22 of the nipple/areola member 16 is positioned adjacent to the nipple and areola shaped region 30. A preferred method of manufacturing the breast prosthesis 10 is discussed in detail below.

The nipple/areola member 16 may be formed of any liquid composition which provides the desired color and hardness (i.e., a color and hardness which simulates the areola and nipple of a human breast) upon curing. The preferred liquid compositions are silicone resin compositions. The formation of the nipple/areola member 16 will be discussed in terns of using this preferred composition, although the invention is not limited thereto. The nipple/areola member 16 can De produced by mixing a silicone resin composition with known pigments so as to match as close as possible the natural color of a woman's nipple and areola. The silicone resin composition used to form the nipple/areola member 16 is selected to simulate the natural texture/hardness of a woman's nipple and areola, and is preferably denser than the composition used to create the gelled body of the prosthesis. A silicone resin composition which has been found to be useful in this application is Dow Corning Sylgard 186 Elastomer. The pigmented silicone resin composition is then mixed with a known solvent.

Figure 2B:
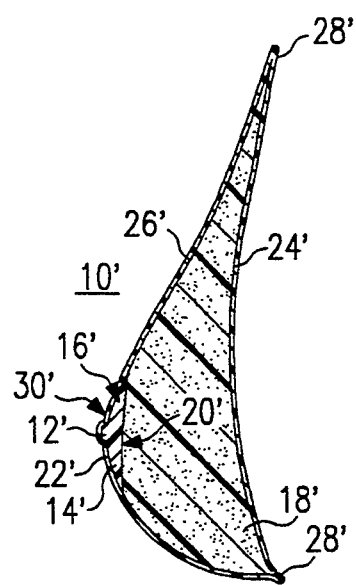
FIG. 2B is a sectional view of the novel breast prosthesis fabricated in accordance with an alternative method of the present invention taken along a line corresponding to line 2a—2a of FIG. 1.
Figure 2A:
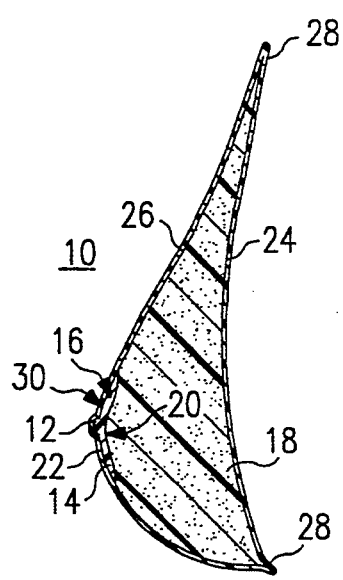
FIG. 2A is a sectional view of the novel breast prosthesis fabricated in accordance with a preferred method of the present invention taken along line 2a—2a of FIG. 1.

Referring to FIG. 2B, there is shown an encapsulated breast prosthesis 10' having a nipple 12', an areola 14' and a color and hardness differentiated areola/nipple member 16'. The nipple/areola member 16' is formed by pouring a liquid composition into a female mold cavity. The nipple/areola member 16' is planar-convex in shape with a planar side 20' adjacent to a gelled body 18' and a convex side 22' facing outward from the gelled body 18'. The convex side 22' is located adjacent to a nipple and areola region 30' of an outer skin 26'. The exterior shape of the prosthesis 10' is defined by inner skin 24' and outer skin 26' which are sealed along their peripheries 28'. The planar-convex nipple/areola member 16' is contrasted to the concave-convex nipple/areola member 16 formed by spraying the composition. It is believed that a planar-convex shape of the nipple/areola member 16' adds significant density and hardness to the finished product which may detract from the desired texture and feel. In contrast, the convex-concave nipple/areola member 16, shown in FIG. 2A, results in a breast prosthesis 10 which more closely simulates the natural feel and texture of the nipple and areola of a woman's breast and is therefore preferred.

Figure 4:
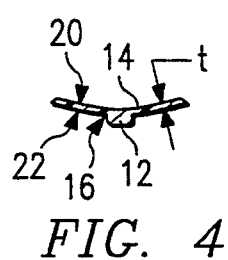
FIG. 4 is a sectional view of the nipple/areola of the breast prosthesis.
Figure 3:
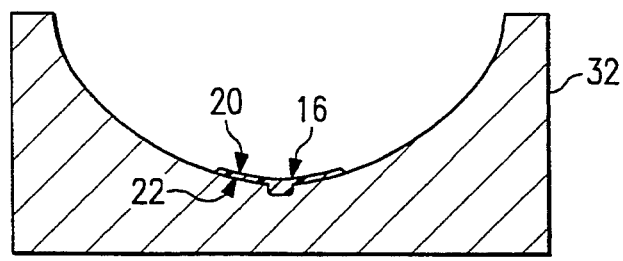
FIG. 3 is a sectional view of a mold used in the formation of the nipple/areola of the breast prosthesis.

Referring to FIGS. 3 and 4, the nipple/areola member 16 is preferably formed by spraying the pigmented silicone resin composition into a female (concave) mold cavity 32. The mold cavity 32 is shaped to correspond with the natural shape of a woman's nipple and areola. The nipple/areola member 16 is gradually built up in thickness by an accumulation of coats of resin, thereby producing a nipple/areola member 16 which is substantially convex-concave. That is, the nipple/areola member 16 has a concave side 20 which will be adjacent to the gelled body 18 (FIG. 2A) and a convex side 22 with a nipple 12 protruding therefrom which will face outward from said gelled body 18 and adjacent to the nipple and areola portion 30 of the outer skin 26 (FIG. 2A). The number of coats of resin to be applied will depend upon the particular feel of the nipple and areola desired by the manufacturer. It has been found that 5 to 15 coats (approximately 0.05 mm per coat) of the above referenced Sylgard Elastomer produce an extremely satisfactory nipple/areola member 16. The preferable thickness t (see FIG. 4) of the nipple/areola member 16 is about 0.50 millimeters in the areola portion 14. The nipple/areola member 16 is then cured at about 100° to 150° F. (about 38° to 66° C.) for approximately one hour. An additional second curing step at about 300° to 400° F. (about 150° to 205° C.) for one to two hours may also be performed if a two textured product is desired, i.e., one side tacky and the other side slick. The nipple/areola member 16 may then be cut to the desired size and shape, preferably circular.

The composition used to form the nipple/areola member 16 may be deposited into a female mold cavity by means other than spraying. For example, the nipple/areola member 16 of the prosthesis may be formed by pouring the silicone resin composition into a female mold cavity rather than by spraying the composition. However, as disclosed above, spraying has a distinct advantage over simply pouring the silicone resin composition into the mold cavity. Specifically, the convex-concave shape of the nipple/areola member 16 (FIG. 2A) formed by spraying results in a breast prosthesis which more closely simulates a human nipple and areola than the convex-planar nipple/areola member 16' formed by pouring (FIG. 2B).

Figure 5:
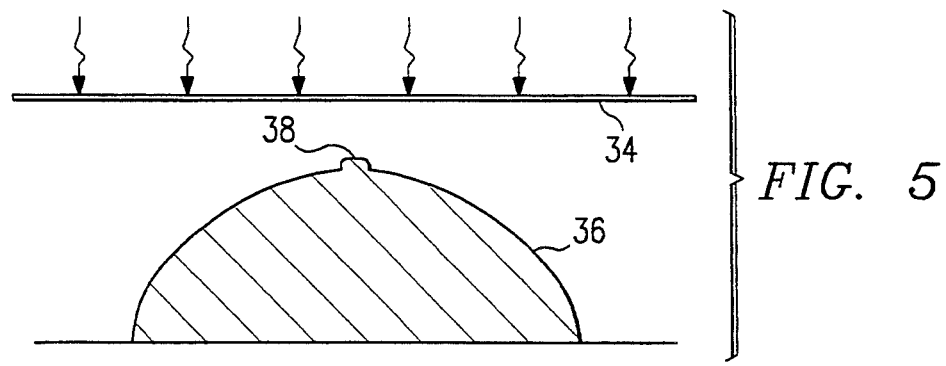
FIGS. 5, 6, 7, and 8 are diagrammatic illustrations depicting the process of fabricating the breast prosthesis.

Referring to FIG. 5, a flexible film 34 of any suitable thermoplastic material is heated and placed on a male (convex) vacuum forming tool or mold 36 in order to form the outer skin 26 of the breast prosthesis 10. The most commonly used and preferred thermoplastic materials are polyurethane based. The male vacuum forming mold 36 is shaped to simulate the natural shape of the female breast and may be of various shapes and sizes in order to produce various sized prostheses. Preferably, the male vacuum forming mold 36 includes a nipple 38 which corresponds to the size and shape of the nipple/areola member 16 described above. This results in an outer skin 26 having a nipple and areola shaped region 30 as shown in FIG. 2A. Alternatively, if a male vacuum forming mold without a nipple 38 is used, a nipple/areola member 16 produced by the above described steps may be placed on the male vacuum forming mold prior to forming the outer skin of the breast form. The heated film 34 is then placed over vacuum forming mold 34 to produce the outer skin 26 with a nipple and areola shaped region 30 as shown in FIG. 2A.

Figure 6:
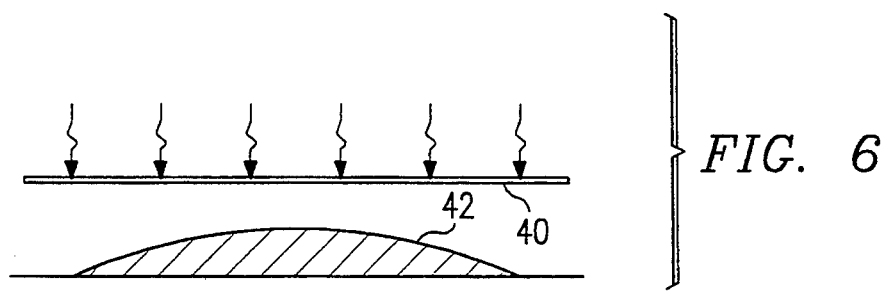

With reference to FIG. 6, the inner skin 24 is also preferably formed by heating and placing a flexible thermoplastic film 40 over a male (convex) vacuum forming mold 42. Preferably, the shape of the male vacuum forming mold 42 is such as to form the inner skin 24 which is concave, thereby resulting in a breast prosthesis which more suitably fits the chest area of the body where the natural breast was removed.

Figure 7:
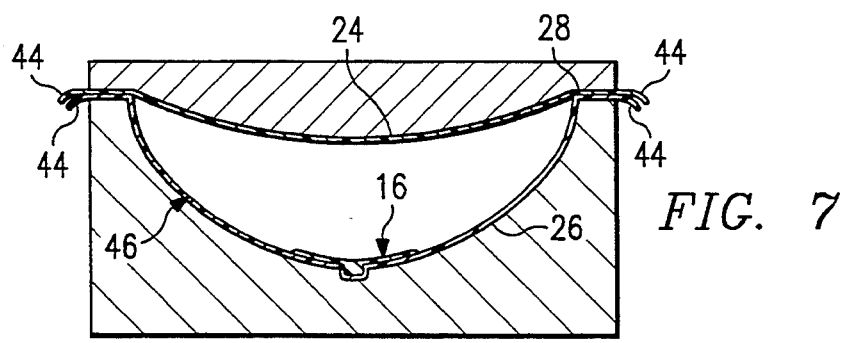

Referring to FIG. 7, the inner skin 24 and the outer skin 26 are then sealed together along their peripheries 28 with the nipple/areola member 16 encapsulated inside. Excess film 44 extends from the sealed peripheries 28. A capsule 46 with the nipple/areola member 16 disposed therein is thereby formed by the inner and outer skins, 24 and 26, respectively. Preferably, the peripheries of the skins 24 and 26 are sealed together by high frequency sealing methods known in the art. For example, a brass high frequency two piece sealing die as shown in FIG. 7 can be used. The die is used in conjunction with a high frequency electronic sealing machine in order to "weld" or seal polyurethane or vinyl film in the configuration of that particular die. These seals are approximately ⅜" wide around the peripheries of the shape desired. The inner and outer film skins, 24 and 26, respectively, are positioned on the bottom sealing die, then the top portion with mylar buffer attached is placed over the skins and bottom portion of the die. The high frequency sealing machine is then activated, effectively sealing or melting the two film skins 24 and 26 together.

Figure 8:
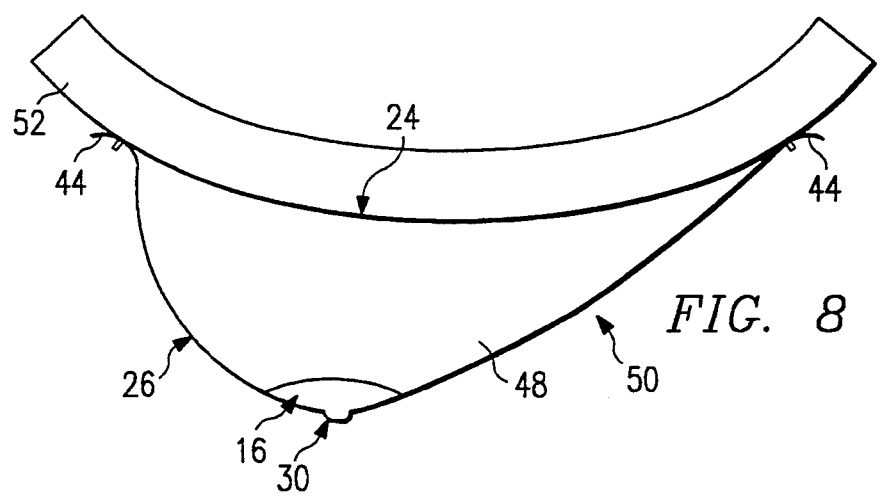

Referring to FIG. 8, the empty capsule 46 (FIG. 7) is then filled with a gel-forming liquid composition 48 through an opening to form a filled capsule 50. The opening may be formed by puncturing a small hole in the wall of the capsule 46 or by leaving a small segment of the respective peripheries of the inner skin 24 and outer skin 26, unsealed. Any trapped air in the filled capsule 50 should be removed before sealing the opening. Trapped air may be removed by use of a vacuum chamber. Any additional air not removed by the vacuum chamber may be removed by mechanical means, such as a syringe. After the trapped air is substantially removed, the opening is sealed.

The next stage in the procedure is the curing step and preparation therefore. The filled capsule 50 is preferably attached to a curved template or radius form 52 with the inner skin 24 abutting the outside radius of the template 52. Referring to FIG. 8, the filled capsule 50 may be attached to the form 52 by pinning it to the form 50 through excess film 44. The template 52 is then inverted as shown in FIG. 8. By inverting the template, the nipple/areola member 16 is allowed to sink through the uncured gel-forming composition 48 and is positioned adjacent to the nipple and areola shaped region 30 of the outer skin 26. The nipple/areola member 16 sinks because it is made of a denser composition than the gel-forming composition 48 used to form the remainder (i.e., the gelled body 18) of the prosthesis 10. A shaping device (not shown) may be attached to the top or convex side of the breast prosthesis 10 as may be required with larger size prostheses. The inverted capsule 50 with the nipple/areola member 16 positioned adjacent to the nipple and areola shaped region 30 of the outer skin 26 may then be placed in an oven where the gel-forming composition 48 is cured to form a gel which comprises the body of the prosthesis 10. After the gel-forming composition 48 has been cured, the excess film 44 can be trimmed from the peripheral edges, thus producing the completed prosthesis 10.

Any suitable gel-forming liquid may be used to form the body of the prosthesis 10, such as liquid resin compositions which cure to a gelatinous state. As used herein the terms "cure" or "curable" (or any variations thereof) are not limited to processes or compositions which require a heating step to form a gelled composition. For example, a composition which forms a gel at room temperature over time is a curable gel-forming composition. Thus, "curing" as used herein refers to the transformation of a liquid to a gel and may take place at room temperature or any other temperature. The liquid composition used should be selected to simulate the natural color, feel and texture of the body of a woman's breast. Further, pigments may be used to achieve the desired color. Gel-forming liquid compositions most suitable for the formation of the body of the prosthesis 10 are silicone resin compositions. A preferred silicone composition for the body of the prosthesis is Applied Silicone Gel 50001 manufactured by Applied Silicone of Ventura, Calif. This silicone resin composition can be cured at a temperature of about 100° to 135° F. (about 38° to 58° C.) for approximately 15 hours and results in an extremely satisfactory prosthesis. Further, to facilitate the bonding of the inner and outer skins to the silicone resin composition 48 upon curing, the exterior of the inner skin 24 and outer skin 26 may be coated with a bonding agent, such as a trimethyl monohydrogen substituted siloxane oligomer mixture.

Those skilled in the art will readily realize that a prosthesis formed in accordance with the method of the present invention, or employing the structure of the present invention, may utilize a wide variety of materials and methods. In any event, the materials, structures and methods, though perhaps not resembling the specific exemplary preferred embodiments described herein, will nevertheless employ the present invention as defined in the following claims.

We claim:
1. An encapsulated breast prosthesis comprising:
   (a) an outer skin of flexible film material having a shape which corresponds to the shape of a human breast including a region which corresponds to the shape of a human nipple and areola, said outer skin having a periphery;
   (b) an inner skin of flexible film material having a periphery, said inner and outer skins being sealed along their peripheries;
   (c) a gelled body disposed between and in contact with said inner and outer skins; and
   (d) a nipple/areola member having a desired color and hardness so as to simulate the natural color and hardness of a nipple and areola of a human breast, said nipple/areola member having a first convex side and a second side, said convex side shaped in the form of said human nipple and areola, said member being disposed between said gelled body and said outer skin with said convex side facing outwardly adjacent to said region of said outer skin which corresponds to the shape of said human nipple and areola and said second side being adjacent to said gelled body.

2. The encapsulated breast prosthesis of claim 1 wherein said inner and outer skins are made of a thermoplastic material.

3. The encapsulated breast prosthesis of claim 2 wherein said thermoplastic material is polyurethane based.

4. The encapsulated breast prosthesis of claim 1 wherein said nipple/areola member is made of a silicone resin composition.

5. The encapsulated breast prosthesis of claim 1 wherein said nipple/areola member has a concave side facing inwardly adjacent to said gelled body.

6. The encapsulated breast prosthesis of claim 1 wherein said gelled body comprises a cured silicone resin composition.

7. The encapsulated breast prosthesis of claim 1 wherein said inner skin has a concave exterior shape corresponding to the area of the human body where the natural breast was removed.

* * * * *